United States Patent [19]

Schickaneder et al.

[11] Patent Number: 4,866,066
[45] Date of Patent: Sep. 12, 1989

[54] THIOMETHYLPYRIDINE DERIVATIVES AND THEIR USE FOR ELICITING A BRONCHOSECRETOLYTIC OR MUCOLYTIC RESPONSE

[75] Inventors: Helmut Schickaneder, Eckental; Heidrun Engler, Cadolzburg; Istvan Szelenyi, Schwaig, all of Fed. Rep. of Germany

[73] Assignee: Ludwig Heumann & Co. GmbH, Nuremberg, Fed. Rep. of Germany

[21] Appl. No.: 15,007

[22] Filed: Feb. 17, 1987

Related U.S. Application Data

[63] Continuation of Ser. No. 490,138, Apr. 29, 1983, abandoned.

[30] Foreign Application Priority Data

May 5, 1982 [DE] Fed. Rep. of Germany ....... 3216843

[51] Int. Cl.⁴ .................. A61K 31/505; C07D 487/06; C07D 401/12; C07D 413/12
[52] U.S. Cl. .................................... 514/274; 514/258; 514/302; 514/312; 514/339; 514/341; 544/253; 544/262; 544/315; 544/318; 546/157; 546/256; 546/270; 546/271; 546/275; 546/276; 546/339
[58] Field of Search ............... 544/315, 318, 262, 253; 514/274, 258

[56] References Cited

FOREIGN PATENT DOCUMENTS

78206/75 8/1976 Australia .

OTHER PUBLICATIONS

Eichler et al., CA 99-70626b.
Schickaneder et al., CA 106-138391s.
Tweit et al., CA 80-420, p. 1974.
Haviv et al., J. Med. Chem., 1983, vol. 26, No. 2, pp. 218-222.
Schickaneder et al., J. Med. Chem., 1987, 30, pp. 547-551.
Schickaneder et al., CA 100-68183a.
Haviv et al., CA 98-46446b.

*Primary Examiner*—Cecilia Shen
*Attorney, Agent, or Firm*—Burns, Doane, Swecker & Mathis

[57] ABSTRACT

Thiomethylpyridine derivatives having bronchosecretolytic and mucolytic activity according to the formula:

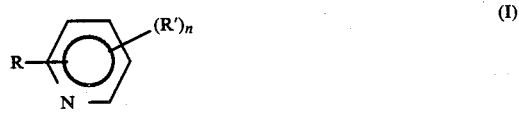

(I)

wherein R is a group attached in the 2-, 3-, or 4-position of the pyridine ring which corresponds to the following general formula:

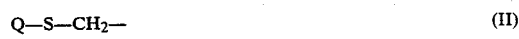

(II)

wherein Q is a substituted or unsubstituted aryl group or a 5- or 6-membered heterocyclic group which may optionally contain one or more substituents and/or which may be condensed with an optionally substituted phenyl group or with an optionally substituted heterocycle; R' is a lower alkyl group, a halogen atom or an aminoalkyl group; and n is 0 or an integer of from 1 to 4; and the therapeutically-acceptable acid addition salts thereof.

The new compounds are distinguished by surprising activity compared with known compounds, such as "Ambroxol".

20 Claims, No Drawings

THIOMETHYLPYRIDINE DERIVATIVES AND THEIR USE FOR ELICITING A BRONCHOSECRETOLYTIC OR MUCOLYTIC RESPONSE

This application is a continuation of application Ser. No. 490,138, filed Apr. 29, 1983, now abandoned.

This invention relates to new thiomethyl pyridine derivatives, to a process for their production and to medicaments containing them.

The new compounds according to the invention are surprisingly distinguished by high bronchosecretolytic and mucolytic activity which may be therapeutically utilized.

It is well known that reducing the viscosity of sputum by medicaments in the treatment of acute and chronic bronchial illnesses (for example infections of the respiratory tracts, asthmatic complaints, obstructive disorders and the like) is an important therapeutic objective. Various kinds of medicaments are known for treating illnesses of this kind. They differ from one another in their local and systemic activity. N-acetyl cysteine inter alia belongs to the group of locally active medicaments. The systemically active types include for example Ambroxol, i.e. trans-4-(2-amino-3,5-dibromobenzyl)-aminocyclohexanol, which is an established bronchosecretolytic agent in the treatment of bronchial disease. This compound is described, for example, in German Patent No. 1,593,579.

The object of the present invention is to provide new bronchosecretolytically and mucolytically active compounds of which the oral and parenteral activity is significantly improved in relation to established compounds acting in the same direction, such as for example Ambroxol.

This object is achieved by the invention.

Accordingly, the present invention relates to new thiomethyl pyridine derivatives corresponding to the following general formula

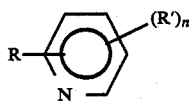 (I)

in which R is a group attached in the 2-, 3- or 4-position of the pyridine ring and corresponding to the following general formula

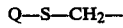 (II)

where

Q is a substituted or unsubstituted aryl group or a 5- or 6-membered heterocyclic group which may optionally be substituted by one or more substituents and/or which may be condensed with an optionally substituted phenyl group or an optionally substituted heterocycle, R' is a lower alkyl group, a halogen atom or an aminoalkyl group and n=0 to 4, and to their therapeutically acceptable acid addition salts.

In general formula I, R is a group attached in the 2-, 3- or 4-position of the pyridine ring and corresponding to the following formula

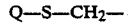 (II)

in which Q is an aryl group, for example a phenyl or naphthyl group. The aryl group may be unsubstituted or substituted by one or more substituents, such as halogen atoms, lower alkyl groups or lower alkoxy groups. Halogen atoms are, for example, fluorine atoms, chlorine atoms, bromine atoms and iodine atoms, chlorine atoms being preferred. Lower alkyl groups are straight-chain or branched-chain alkyl groups containing from 1 to 4 carbon atoms, such as for example methyl groups, ethyl groups, isopropyl groups and butyl groups. Lower alkoxy groups contain from 1 to 4 carbon atoms in the alkyl chain. Examples of lower alkoxy groups are methoxy groups, ethoxy groups, propoxy groups and butoxy groups. One preferred example of a substituted aryl group is a phenyl group which is substituted in the p-position by a halogen atom, preferably a chlorine atom, by a lower alkyl group, preferably a methyl group, or by a lower alkoxy group, preferably a methoxy group.

In addition, Q may be a 5- or 6-membered heterocyclic group which may be substituted by one or more substituents and/or which may be condensed with an optionally substituted phenyl group or an optionally substituted heterocycle. Practical examples of a heterocyclic group such as this are the imidazolyl group, thiazolyl group, thienyl group, oxazolyl group, pyrimidinyl group or pyridyl group. The heterocyclic group may contain one or more substituents. Examples of the substituents in question are lower alkyl groups, halogen atoms and alkoxy groups. Lower alkyl groups are linear or branched carbon chains containing from 1 to 4 carbon atoms, such as for example methyl groups, ethyl groups, isopropyl groups or butyl groups. Halogen atoms are, for example, fluorine atoms, chlorine atoms, bromine atoms and iodine atoms. Lower alkoxy groups are methoxy groups, ethoxy groups, propoxy groups and butoxy groups.

The 5- or 6-membered heterocyclic group may in addition be condensed with an optionally substituted phenyl group or an optionally substituted heterocycle. The optionally substituted heterocycle may be, for example, pyridine, pyrimidine or thiazole. The phenyl group and the heterocycle may be substituted, preferably by a halogen atom, preferably a chlorine atom, by a lower alkyl group, preferably a methyl group, or by a lower alkoxy group, preferably a methoxy group.

As mentioned above, the group R may be attached in the 2-, 3- or 4-position of the pyridine ring, the 3-position being preferred.

In general formula I, R' is a lower alkyl group (as defined above), a halogen atom (as defined above) or an aminoalkyl group (the alkyl group preferably being a lower alkyl group). n has a value of from 0 to 4. Where n=0, the pyridine ring, apart from the substituent R, is unsubstituted. Where n=1, the pyridine ring carries a substituent R' which is preferably attached in the 6-position of the pyridine ring. Where n=2, two groups R' are present, preferably being attached in the 5-position and 6-position of the pyridine ring. As for the rest, the pyridine ring may be substituted by the radical R' irrespective of the position of the nitrogen atom.

The compounds corresponding to general formula I readily from acid addition salts, for example mono-, di- and tri-addition salts, such as for example hydrochlorides, hydrobromides, sulfates, acetates, maleates, fumarates, oxalates, succinates and embonates, etc.

The compounds according to the invention may be produced by a process which is characterized in that, using methods known per se, a thiolate corresponding to the following general formula Q-SMe  (III)

in which Q is as defined above and Me is an alkali atom, is reacted with a picolyl chloride hydrohalide corresponding to the following general formula

(IV)

in which Hal is a halogen atom and in which the chloromethyl group is in the 2-, 3- or 4-position of the pyridine ring and R' and n are as defined above, in an aqueous-alcoholic alkali hydroxide solution in which the alkali hydroxide is present in an excess over and above the stoichiometric quantity and the free base thus obtained is optionally converted into a therapeutically acceptable acid addition salt.

In formula III, Me is an alkali atom, for example a potassium or sodium atom, a sodium atom being preferred. In general formula IV, Hal is a halogen atom, for example a chlorine or bromine atom, preferably a chlorine atom. The reaction is carried out in an aqueous-alcoholic alkali hydroxide solution in which the alkali hydroxide is present in an excess over and above the stoichiometric quantity, preferably in at least twice the equimolar quantity. The aqueous-alcoholic solution is preferably an aqueous-ethanolic-solution. The preferred alkali hydroxide is sodium hydroxide. The reaction is best carried out by dissolving the thiolate corresponding to general formula III in the aqueous-alcoholic alkali hydroxide solution at a temperature of from 0° to 5° C. and subsequently reacting the resulting solution for 2 to 6 hours and preferably for 4 hours at room temperature with an equimolar quantity of the picolyl chloride hydrohalide compound dissolved in aqueous-alcoholic and preferably aqueous-ethanolic solution.

Because the alkali hydroxide is used in a stoichiometric excess, the free base is obtained and may be subsequently converted into a therapeutically acceptable salt in the usual way by reaction with a pharmaceutically acceptable acid.

The compounds according to the invention are distinguished by a surprisingly improved bronchosecretolytic and mucolytic activity so that they may be used for therapy in considerably smaller quantities than known active substances.

Accordingly, the present invention also relates to a pharmaceutical preparation or medicament having bronchosecretolytic and mucolytic activity which, in addition to standard auxiliaries and vehicles, contains at least one thiomethyl pyridine derivative corresponding to general formula I.

The pharmaceutical preparation according to the invention may be used for all types of bronchial illness, for example acute and chronic respiratory disease, for post-operative treatment of the respiratory tracts and also in all processes where it is desirable to reduce the viscosity of bronchial mucus.

The compound used in accordance with the invention is preferably orally administered. The oral daily dose usually amounts to between 0.01 and 0.2 g and preferably to between 0.02 and 0.1 g which may be administered in one or more daily doses. It may be necessary in individual cases to administer larger or smaller doses in dependence upon the reaction of the individual to the active substance or its formulation and to the time at which or period over which it is administered. For example, there are cases where the compound used in accordance with the invention may be effectively administered in less than the minimum quantity indicated above, whereas in other cases the upper limit specified has to be exceeded. In cases where relatively large quantities are administered, it may be advisable to divide them into several individual doses for daily administration.

For oral administration, the active substance may be formulated for example as capsules produced by conventional methods using pharmaceutically acceptable excipients, for example binders (such as pregelatinized cornstarch, polyvinyl pyrrolidone or hydroxy propylmethyl cellulose); fillers (such as lactose, microcrystalline cellulose or calcium phosphate); lubricants (such as magnesium stearate, talcum or silica); disintegrating agents (for example potato starch or sodium starch glycolate); or moistening agents (for example sodium lauryl sulfate). The capsules may be coated by known methods. Liquid preparations for oral administration or for direct instillation may assume the form of solutions, syrups or suspensions for example or may be presented as a dry product for reconstitution before use either with water or with any other suitable vehicle. Liquid preparations such as these may be prepared by conventional methods using pharmaceutically acceptable additives, for example suspending agents (such as sorbitol syrup, methyl cellulose or hydrogenated edible fats); emulsifiers (for example lecithin or acacia); nonaqueous vehicles (for example almond oil, oily esters or ethyl alcohol); and preservatives (for example methyl or propyl-p-hydroxybenzoates or sorbic acid).

For buccal administration, the preparations may be presented in the form of tablets or lozenges formulated in the usual way.

The compound used in accordance with the invention may be formulated for parenteral administration by injection or for infusion. Preparations for injection may be presented in unit dose form, for example in ampoules or in multi-dose containers, with an added preservative. The preparations may also assume such forms as suspensions, solutions or emulsions in oily or aqueous vehicles and may contain formulating agents, such as suspending agents, stabilizing agents and/or dispersants. Alternatively, the active substance may even be presented in powder form for reconstitution before use with a suitable vehicle, for example sterile, pyrogen-free water.

For administration by inhalation, the compound according to the invention is suitably applied in the form of an aerosol spray from pressurized packs or atomizers using a suitable propellent, for example dichlorodifluoromethane, trichlorofluoromethane, dichlorotetrafluoroethane, carbon dioxide or any other suitable gas. In the case of a pressurized aerosol, the unit dose may be determined by the provision of a valve for releasing a measured quantity.

Pharmacological studies have shown that the thiomethyl pyridine derivatives used in accordance with the invention have superior bronchosecretolytic and mucolytic properties to the known comparison product Ambroxol. The following individual studies were carried out:

1. PHARMACODYNAMICS

1.1 Secretostimulating activity

Bronchosecretolytically active compounds promote the tracheal secretion of phenol red (Chronic Bronchitis Research Group, Chinese Medical Journal 3 : 259, 1977). The increase in the tracheal secretion of phenol red is a measure of bronchosecretolytic activity. The relevant activity of the test substances was studied after oral administration to non-anaesthetized mice. The $ED_{50}$-values indicated in Table I were calculated using the regression curves. As can be seen from the Table, 2-(pyridyl-3-methylthio)-pyrimidine hydrochloride showed the strongest activity. Its effect in promoting the secretion of phenol red was approximately 160 times stronger than that of the known bronchosecretolytic, Ambroxol.

TABLE I

| Compound | $ED_{50}$ (mg/kg) |
|---|---|
| Ambroxol | 250 |
| Example 1 | 1.5 |
| Example 2 | 400 |
| Example 7 | 15 |
| Example 9 | 45 |
| Example 8 | 15 |
| Example 5 | 2.1 |
| Example 6 | 6.3 |
| Example 3 | 10 |
| Example 4 | 12 |
| Example 10 | 12 |

1.2 Mucosecretolytic activity in dogs

Bronchial mucus was removed by means of a bronchoscope from anaesthetized mongrel dogs immediately before and 1 hour after intravenous administration of the test substances and taken up in phosphate buffer. After dialyzation and freeze-drying, the mucus samples were taken up in 0.1M tris-buffer (pH 7) (final concentration 1% w/v). Viscosity was measured by means of a rotary viscosimeter (as manufactured by Contraves, Stuttgart).

As can be seen from Table II, the known bronchosecretolytic, Ambroxol, produced a distinct reduction in the viscosity of the bronchial mucus. The identical quantity by weight of 2-(pyridyl-3-methylthio)-pyrimidine hydrochloride produced an even more distinct reduction in the viscosity of the bronchial mucus.

TABLE II

| Compound | Dose and administration route | Initial value | Viscosity mPa × s 1 hour after administration |
|---|---|---|---|
| Control (0.9% of NaCl) | i.v | 4.2 (3.6–4.8) | 4.8 (4.4–5.2) |
| Example 1 | 10 mg/kg i.v. | 3.9 (3.2–4.5) | 1.2 (1.0–1.4) |
| Ambroxol | 10 mg/kg i.v. | 3.8 (3.6–4.0) | 2.3 (1.4–3.2) |

2. Toxicologic results

The compounds according to the invention show low oral toxicity in acute tests. Thus, 2-(pyridyl-3-methylthio)-pyrimidine hydrochloride was found to have an $LD_{50}$-value in mice of 1156 mg/kg p.o. Under identical conditions, Ambroxol proved to be slidingly less toxic ($LD_{50}$: 2720 mg/kg p.o. according to Puschmann et al, Arzn. Forsch. 28 : 889, 1978).

The invention is illustrated by the following Examples.

EXAMPLE 1

Production of 2-(pyridyl-3-methylthio)-pyrimidine hydrochloride

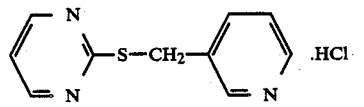

8.4 g (0.21) mole of sodium hydroxide dissolved in 120 ml of water are added dropwise at 0° C. to a solution of 11.2 g (0.1 mole) of 2-mercaptopyrimidine in 250 ml of ethanol. 16.4 g (0.1 mole) of 3-picolyl chloride hydrochloride dissolved in 100 m loof water are then slowly added, followed by stirring for 4 hours at room temperature. The reaction solution is concentrated, taken up in 500 ml of ether, the organic phase is washed 3 times with 100 ml of water, dried over sodium sulfate, filtered and the filtrate concentrated in vacuo. The solid accumulating, which represents the base, is recrystallized from hexane.

Colorless crystals melting at 53° to 54° C.; $R_f=0.5$ ($CH_2Cl_2$/MeOH 9/1); Yield 9.14 g (45%).

$C_{10}H_9N_3S$ (203) calculated: C 59.09 H 4.46 N 20.67 S 15.77; observed: C 59.20 H 4.47 N 20.65 S 15.73.

$^1$H-NMr-spectrum ($CDCl_3$): $\delta=4.40$ (s) ($-SCH_2-$)2 H, 7.0 (t) (aromatics-H) 1H, 7.20 (m) (aromatics-H) 1H, 7.80 (d) (aromatics-H) 1H, 8.53 (m) (aromatics-H) 3H, 8.73 (s) (aromatics-H) 1H ppm.

The hydrochloride is prepared by adding an equimolar 10% ethanolic HCl-solution to an ethereal solution of 2-(pyridyl-3-methylthio)-pyrimidine. The hydrochloride accumulates in analytically pure form.

Colorless crystals melting at 134° to 135° C.; $R_f=0.85$ ($CH_2Cl_2$/MeOH, 8/2, $NH_3$-vapors); Yield (quant.).

$C_{10}H_{10}ClN_3S$ (240) calculated: C 50.10 H 4.20 N 17.53 S 13.37; observed: C 50.18 H 4.10 N 17.45 S 13.36.

$^1$H-NMR-spectrum ($D_2O$): $\delta=5.03$ (s) ($-S-CH_2$) 2H, 7.70 (t) (aromatics-H) 1H, 8.43 (m) (aromatics-H) 1H, 9.03 (d) (aromatics-H) 2H, 9.13 (t) (aromatics-H) 2H, 9.37 (s) (aromatics-H) 1H ppm

EXAMPLE 1a

Production of 2-(pyridyl-3-methylthio)-pyrimidine succinate

The succinate is prepared by adding an equimolar ethanolic succinic acid solution to an ethanolic solution of 2-(pyridyl-3-methylthio)-pyrimidine. After concentration of the reaction solution, the succinate accumulates in analytically pure form.

Colorless crystals melting at 98° C. $R_f=0.78$ ($CH_2Cl_2$/MeOH 8/2, $NH_3$-vapors); Yield: (quant.);

$C_{14}H_{15}N_3O_4S$ (321) calculated: C 52.33 H 4.71 N 13.08 S 9.98; observed: C 52.31 H 4.78 N 13.06 S 9.92.

$^1$H-NMR-spectrum ($d_6$-DMSO) $\delta=2.40$ (s) ($-CH_2-CH_2-$) 4H, 4.43 (s) ($S-CH_2$) 2H, 7.27 (t) (aromatics-H) 1H, 7.37 (m) (aromatics-H) 1H, 7.87 (d) (aromatics-H) 1H, 8.47 (d) (aromatics-H) 1H, 8.67 (m) (aromatics-H) 3H ppm.

EXAMPLE 2

Production of 2-(pyridyl-2-methylthio)-pyrimidine hydrochloride

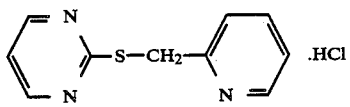

This compound is produced as in Example 1 from 2-mercaptopyrimidine and 2-picolyl chloride hydrochloride.

Colorless crystals melting at 163° to 164° C.;
$R_f=0.85$ (CH$_2$Cl$_2$/MeOH, 8/2, NH$_3$-vapors); Yield 14.3 g (60%).
C$_{10}$H$_{10}$ClN$_3$S (240) calculated: C 50.10 H 4.20 N 17.53 S 13.37; observed: C 50.02 H 4.23 N 17.39 S 13.54.
$^1$H-NMR-spectrum (D$_2$O): $\delta=5.13$ (s) (S-CH$_2$) 2H, 7.67 (t) (aromatics-H) 1H, 8.37 (t) (aromatics-H) 1H, 8.53–9.27 (m) (aromatics-H) 5H ppm.

EXAMPLE 3

Production of 2-(pyridyl-3-methylthio)-4-methyl-pyrimidine hydrochloride

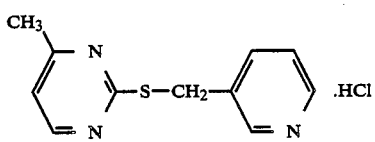

This compound is produced as in Example 1 from 2-mercapto-4-methyl pyrimidine and 3-picolyl chloride hydrochloride.

Colorless crystals melting at 154° C.;
$R_f=0.8$ (CH$_2$Cl$_2$/MeOH, 8/2, NH$_3$-vapors); Yield 10.9 g (43%)
C$_{11}$H$_{12}$ClN$_3$S (254) calculated: C 52.07 H 4.77 N 16.56 S 12.63; observed: C 52.18 H 4.81 N 16.58 S 12.55.
$^1$H-NMR-spectrum (D$_2$O): $\delta=2.80$ (2) (CH$_3$) 3H, 4.93 (s) (S—CH$_2$) 2H, 7.43 (d) (aromatics-H) 1H, 8.47 (t) (aromatics-H) 1H, 8.73 (d) (aromatics-H) 1H, 9.17 (m) (aromatics-H) 2H, 9.47 (s) (aromatics-H) 1H ppm.

EXAMPLE 4

Production of 2-(pyridyl-3-methylthio)-4,6-dimethyl-pyrimidine hydrochloride

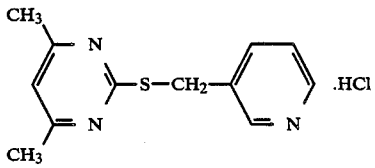

This compound is produced as in Example 1 from 4,6-dimethyl-2-mercaptopyrimidine and 3-picolyl chloride hydrochloride.

Colorless crystals melting at 155° to 156° C.;
$R_f=0.8$ (CH$_2$Cl$_2$/MeOH, 8/2, NH$_3$-vapors); Yield 10.2 g (38%);
C$_{12}$H$_{14}$ClN$_3$S (268) calculated: C 53.83 H 5.27 N 15.69 S 11.97, observed: C 53.79 H 5.37 N 15.70 S 11.93.
$^1$H-NMR-spectrum (D$_2$O): $\delta=2.73$ (s) (2×CH$_3$) 6H, 4.90 (s) (S—CH$_2$) 2H, 7.20 (s) (aromatics-H) 1H, 8.43 (t) (aromatics-H) 1H, 8.83 (d) (aromatics-H) 2H, 9.13 (s) (aromatics-H) 1H ppm.

EXAMPLE 5

Production of 2-(pyridyl-3-methylthio)-pyridine dihydrochloride

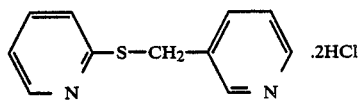

This compound is produced as in Example 1 from 2-mercaptopyridine and 3-picolyl chloride hydrochloride.

Colorless crystals melting at 149° to 152° C.;
$R_f=0.75$ (CHCl$_3$/ C$_2$H$_5$OH, 8/2, NH$_3$-vapors); Yield 5.9 g (25%).
C$_{11}$H$_{12}$Cl$_2$N$_2$S (239) calculated: C 48.16 H 4.38 S 11.68; observed: C 48.28 H 4.32 S 11.53.
$^1$H-NMR-spectrum (D$_2$O): $\delta=5.30$ (s) (S-CH$_2$) 2H, 8.13–9.33 (aromatics-H) 7H, 9.50 (s) (aromatics-H) 1H ppm.

EXAMPLE 6

Production of 2-(pyridyl-2-methylthio)-pyridine dihydrochloride

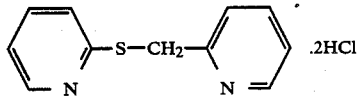

This compound is produced as in Example 1 from 2-mercaptopyridine and 2-picolyl chloride hydrochloride.

Colorless crystals melting at b 106° to 108° C.;
$R_f=0.75$ (CHCl$_3$/C$_2$H$_5$OH, 8/2, NH$_3$-vapors); Yield 6.7 g (28%)
C$_{11}$H$_{12}$Cl$_2$N$_2$S (239) calculated: C 48.16 H 4.38 S 11.68; observed: C 45.99 H 4.71 S 11.04.
$^1$H-NMR-spectrum (D$_2$O): $\delta=5.37$ (s) (—S—CH$_2$) 2H, 8.17–9.37 (m) (aromatics-H) 8H ppm

EXAMPLE 7

Production of 2-(methylthio-3-pyridyl)-benzoxazole

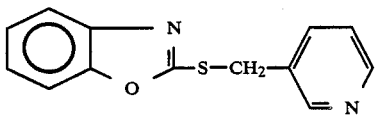

This compound is produced as in Example 1 from 2-mercaptobenzoxazole and 3-picoyl chlorides hydrochloride.

Colorless crystals melting at 88° C.;
$R_f=0.85$ (CH$_2$Cl$_2$/CH$_3$OH, 85/15); Yield 11.1 g (46%).
C$_{13}$H$_{10}$N$_2$OS (242)

¹H-NMR-spectrum (CDCl₃): δ=4.5 (s) (S—CH₂) 2H, 7.13–7.93 (m) (aromatics-H) 6H, 8.53 (d) (aromatics-H) 1H, 8.80 (s) (aromatics-H) 1H ppm.

EXAMPLE 8

Production of 6-methyl-2-(methylthio-3-pyridyl)-benzoxazole hydrochloride

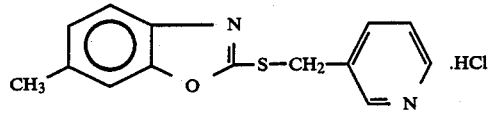

This compound is produced as in Example 1 from 6-methyl-2-mercaptobenzoxazole and 3-picoyl chloride hydrochloride.

Colorless crystals melting at 182° to 183° C.;
R$_f$=0.86 (CH₂Cl₂/MeOH, 8/2, NH₃-vapors); Yield 18.4 g (63%).
C₁₄H₁₃ClN₂OS (293) calculated: C 57.43 H 4.48 N 9.57; observed: C 57.49 H 4.57 N 9.57.
¹H-NMR-spectrum (D₂O): δ=2.53 (s) (—CH₃) 3H, 5.00 (s) (S—CH₂) 2H, 7.20–7.67 (m) (aromatics-H) 3H, 8.40 (m) (aromatics-H) 1H, 9.10 (m) (aromatics-H) 2H, 9.33 (s) (aromatics-H) 1H ppm.

EXAMPLE 9

Production of 2-(methylthio-2-pyridyl)-benzoxazole oxalate

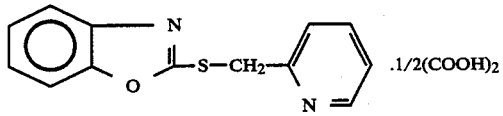

This compound is produced as in Example 1 from 2-mercaptobenzoxazole and 2-picolyl chloride hydrochloride. The oxalate is formed with half the equimolar quantity of oxalic acid in acetone.

Colorless crystals melting at 98° to 102° C.;
R$_f$=0.4 (CH₂Cl₂/CH₃OH, 95/5); Yield 12.3 g (43%).
C₁₄H₁₁N₂O₃S (287) calculated: C 58.53 H 3.86; observed: C 58.46 H 3.89.
¹H-NMR-spectrum (CD₃OD): δ=4.67 (s) (S—CH₂) 2H, 7.73–8.00 (m) (aromatics-H) 7H 8.50 (d) (aromatics-H) 1H ppm.

EXAMPLE 10

Production of 2-(methylthio-3-pyridyl)-oxazolo(4,5-c) pyridine dihydrochloride

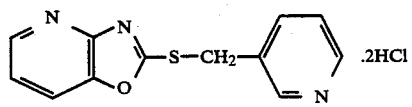

This compound is produced as in Example 1 from 2-mercapto-oxazolo(4,5-c) pyridine and 3-picolyl chloride hydrochloride.

Colorless crystals melting at 183° to 185° C.;
R$_f$=0.77 (CH₂Cl₂/MeOH, 8/2, NH₃-vapors); Yield 17.4 g (55%).

C₁₂H₁₁Cl₂N₃OS (316) calculated: C 45.58 H 3.51 N 13.29 S 10.14; observed: C 45.04 H 3.52 N 12.91 S 10.05.
¹H-NMR-spectrum (D₂O): δ=5.40 (s) (S—CH₂) 2H, 8.03–9.47 (m) (aromatics-H) 6H, 9.60 (s) (aromatics-H) 1H ppm.

EXAMPLE 11

Production of phenyl-3-methylthiopyridine hydrochloride

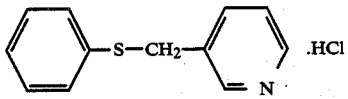

This compound is produced as in Example 1 from thiophenol and 3-picolyl chloride hydrochloride.

Colorless crystals melting at 112° to 115° C.;
R$_f$=0.72 (MeOH, NH₃-vapors); Yield 13.1 g (55%).
C₁₂H₁₂ClNS (238) calculated: C 60.62 H 5.09 N 5.89 S 13.48; Observed: C 60.52 H 5.03 N 5.88 S 13.49.
¹H-NMR-spectrum (D₂O): δ=4.73 (s) (S—CH₂) 2H, 7.43–9.23 (m) (aromatics-H) 9H ppm.

EXAMPLE 12

Production of 4-tolyl-3-methylthiopyridine hydrochloride

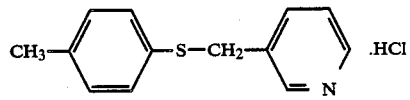

This compound is produced as in Example 1 from p-methylthiophenol and 3-picolyl chloride hydrochloride.

Colorless crystals melting at 148° to 149° C.;
R$_f$=0.71 (MeOH, NH₃-vapors); Yield 11.8 g (47%).
C₁₃H₁₄ClNS (252) calculated: C 62.02 H 5.61 N 5.56; observed: C 62.08 H 5.55 N 5.61.
¹H-NMR-spectrum (D₂O): δ=2.57 (s) (—CH₃) 3H, 4.67 (s) (S—CH2) 2H, 7.47 (s) (aromatics-H) 4H, 8.17–9.24 (m) (aromatics-H) 4H ppm.

EXAMPLE 13

Production of 2-(pyridyl-4-methylthio)-pyrimidine hydrochloride

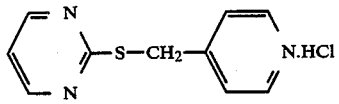

This compound is produced as in Example 1 from 2-mercaptopyrimidine and 4-picolyl chloride hydrochloride.

Colorless crystals melting at 170° to 173° C.;
R$_f$=0.66 (MeOH, NH₃-vapors); Yield 10.3 g (43%)
C₁₀H₁₀ClN₃S (240) calculated: C 50.11 H 4.20 H 17.53 S 13.37; observed: C 50.22 H 4.20 N 17.57 S 13.42.
¹H-NMR-spectrum (D₂O): δ=5.10 (s) (S—CH₂) 2H, 7.53–9.43 (m) (aromatics-H) 7H ppm.

EXAMPLE 14

Production of 4-chlorophenyl-3-methylthiopyridine hydrochloride

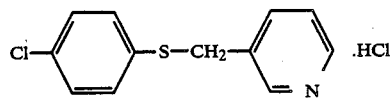

This compound is produced as in Example 1 from 4-chlorothiophenol and 3-picolyl chloride hydrochloride.

Colorless crystals melting at 152° to 153° C.;
$R_f$=0.58 (MeOH, $NH_3$-vapors); Yield 18.5 g (68%).
$C_{12}H_{11}Cl_2NS$ (272) calculated: C 52.95 H 4.07 N 5.15, observed: 52.95 H 4.10 N 5.32.
$^1$H-NMR-spectrum ($D_2O$): δ=4.73 (s) (S-CH2) 2H, 7.47 (s) (aromatics-H) 4H, 8.20–9.30 (m) (aromatics-H) 4H ppm.

EXAMPLE 15

Production of 2-(pyridyl-6-methyl-3-methylthio)-pyrimidine succinate

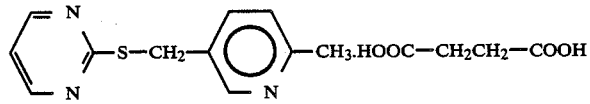

This compound is produced as in Example 1 from 2-mercaptopyrimidine and 6-methyl-3-picolyl chloride hydrochloride.

Colorless crystals melting at 110° to 111° C.;
$R_f$=0.63 ($CH_2Cl_2$/MeOH, 95/5, $NH_3$-vapors); Yield: 12.4 g (37%).
$C_{15}H_{17}N_3O_4S$ (335) calculated: C 53.72 H 5.11 N 12.53; observed: C 53.63 H 5.19 N 12.48.
$^1$H-NMR-spectrum ($d_6$-DMSO): δ=2.43 (s) (—CH$_2$—CH$_2$—) (—CH$_3$) 7H, 4.40 (s) (S-CH2) 2H, 7.10–7.33 (m) (aromatics-H) 2H, 7.77 (d) (aromatics-H) 1H, 8 50 (s) (aromatics-H) 1H, 8.67 (d) (aromatics-H) 2H ppm.

EXAMPLE 16

Production of 3-methoxyphenyl-3-methylthiopyridine hydrochloride

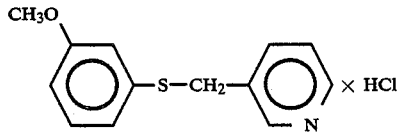

This compound is produced as in Example 1 from 3-methoxy thiophenol and 3-picolyl chloride hydrochloride.

Colorless crystals melting at 130° to 131° C.;
$R_f$=0.75 ($CH_2Cl_2$/MeOH, 95/5, $NH_3$-vapors); Yield: 14.9 g (56%);
$C_{13}H_{14}ClNSO$ (267);
$^1$H-NMR-spectrum ($d_6$-DMSO): δ=3.73 (s) (—OCH$_3$) 3H, 4.50 (s) (S—CH$_2$) 2H, 6.67–7.37 (m) (aromatics-H) 4H, 8.00 (dd) (aromatics-H) 1H, 8.50 (d) (aromatics-H) 1H, 8.87 (m) (aromatics-H) 2H ppm.

EXAMPLE 17

Production of 2-(pyridyl-2-chloro-3-methylthio)-pyrimidine

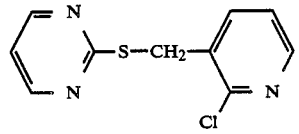

This compound is produced as in Example 1 from 2-mercaptopyrimidine and 2-chloro-3-picolyl chloride hydrochloride.

Colorless crystals melting at 96° to 97° C.;
$R_f$=0.69 ($CH_2Cl_2$/MeOH, 9/1); Yield: 15.1 g (64%).
$C_{10}H_8ClN_3S$ (238); $^1$H-NMR-spectrum (CDCl$_3$): δ=4.50 (s) (S—CH$_2$) 2H, 6.97 (t) (aromatics-H) 1H, 7.13 (dd) (aromatics-H) 1H, 7.90 (d) (aromatics-H) 1H, 8.23 (d) (aromatics-H) 1H, 8.50 (d) (aromatics-H) 2H ppm.

EXAMPLE 18

Production of 2-(pyridyl-3-methylthio)-benzimidazole dihydrochloride

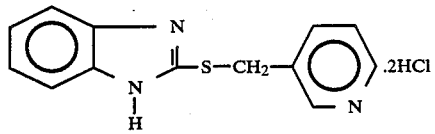

This compound is produced as in Example 1 from 2-mercaptobenzimidazole and 3-picolyl chloride hydrochloride.

Colorless crystals melting at 211° to 213° C.;
$R_f$=0.62 ($CH_2Cl_2$/MeOH, 95/5, $NB_3$-vapors); Yield: 18.2 g (58%).
$C_{13}H_{13}Cl_2N_3S$ (314);
$^1$H-NMR-spectrum ($d_6$-DMSO): δ=5.17 (s) (S—CH$_2$) 2H, 7.20–8.17 (m) (aromatics-H) 5H, 8.63–8.87 (m) (aromatics-H) 2H, 9.10 (s) (aromatics-H) 1H ppm.

EXAMPLE 19

Production of 2-(pyridyl-3-methylthio)-4,5-diphenyl oxazole hydrochloride

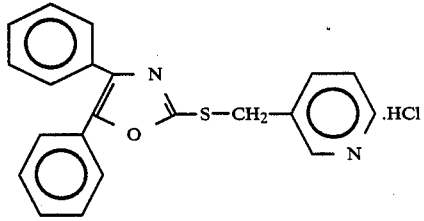

This compound is produced as in Example 1 from 2-mercapto-4,5-diphenyloxazole and 3-picolyl chloride hydrochloride.

Colorless crystals melting at 156° to 157° C.;

$R_f=0.62$ ($CH_2Cl_2$/MeOH, 95/5, $NH_3$-vapors); Yield: 17.9 g (47%).

$C_{21}H_{17}ClN_2OS$ (381) calculated: C 66.22 H 4.50 N 7.35; observed: C 66.23 H 4.50 N 7.47.

$^1$H-NMR-spectrum (d$_4$-MeOH): $\delta=4.73$ (s) (S—CH$_2$) 2H, 7.20–7.67 (aromatics-H) 10H, 8.13 (t) (aromatics-H) 1H, 8.73–9.0 (m) (aromatics-H) 2H, 9.10 (s) (aromatics-H) 1H ppm.

EXAMPLE 20

Production of 2-(pyridyl-3-methylthio)-quinoline dihydrochloride

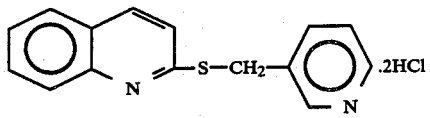

This compound is produced as in Example 1 from 2-mercaptoquinoline and 3-picolyl chloride hydrochloride.

Colorless crystals melting at 173° to 175° C.;

$R_f=0.71$ ($CH_2Cl_2$/MeOH, 95/5, $NH_3$-vapors); Yield: 16.9 g (52%).

$C_{15}H_{14}Cl_2N_2S$ (325) calculated: C 55.39 H 4.34 S 9.86; observed: C 55.26 H 4.36 S 9.36. $^1$H-NMR-spectrum (D$_2$O): $\delta=5.30$ (s) (S-CH$_2$) 2H, 7.70–9.70 (m) (aromatics-H) 10H ppm.

EXAMPLE 21

Production of 2-(pyridyl-3-methylthio)-1-methylimidazole dihydrochloride

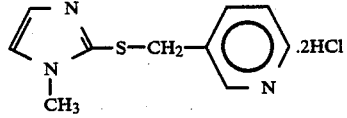

This compound is produced as in Example 1 from 2-mercapto-1-methylimidazole and 3-picolyl chloride hydrochloride.

Colorless crystals melting at 187° to 189° C.;

$R_f=0.43$ ($CH_2Cl_2$/MeOH, 95/5, $NH_3$-vapors); Yield: 12.0 g (43%).

$C_{10}H_{15}Cl_2N_3S$ (280) calculated: C 42.86 H 5.40 N 15.00; observed: C 43.08 H 4.77 N 15.03.

$^1$H-NMR-spectrum (D$_2$O): $\delta=4.43$ (s) (N—CH$_3$) 3H, 5.13 (s) (S—CH$_2$) 2H, 8.00–9.53 (m) (aromatics-H) 6H ppm.

EXAMPLE 22

Production of 2-(pyridyl-3-methylthio-6-chloro)-pyrimidine

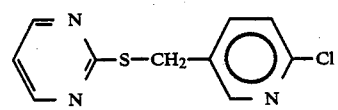

This compound is produced as in Example 1 from 2-mercaptopyrimidine and 6-chloro-3-picolyl chloride hydrochloride.

Colorless crystals melting at 89° to 90° C.;

$R_f=0.68$ ($CH_2Cl_2$/MeOH, 9/1); Yield: 10.0 g (42%), $C_{10}H_8ClN_3S$ (238). $^1$H-NMR-spectrum (CDCl$_3$): $\delta=4.33$ (s) (S—CH$_2$) 2H, 7.00 (t) (aromatics-H) 1H, 7.20 (d) (aromatics-H) 1H, 7.77 (dd) (aromatics-H) 1H, 8.50 (m) (aromatics-H) 3H ppm.

EXAMPLE 23

Production of 4-(pyridyl-3-methylthio)-1-H-pyrazolo(3,4-d)-pyrimidine

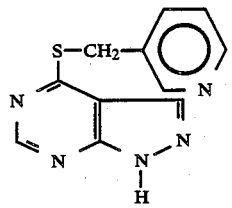

This compound is produced as in Example 1 from 4-mercapto-1-H-pyrazolo-(3,4-d)-pyrimidine and 3-picolyl chloride hydrochloride.

Colorless crystals melting at 148° to 149° C.;

$R_f=0.54$ ($CH_2Cl_2$/MeOH, 9/1); Yield: 16.0 g (66%).

$C_{11}H_9N_5S$ (243) calculated: C 54.31 H 3.73 N 28.79; observed: C 54.27 H 3.77 N 28.75. $^1$H-NMR-spectrum (d$_6$-DMSO): $\delta=4.70$ (s) (S—CH$_2$) 2H, 7.33 (dd) (aromatics-H) 1H, 8.27 (s) (aromatics-H) 1H, 8.50 (d) (aromatics-H) 1H, 8.73 (s) (aromatics-H) 1H, 8.83 (s) (aromatics-H) 1H, 14.13 (s) (N-H) 1 H (exchangeable for D$_2$O) ppm.

EXAMPLE 24

Production of soft gelatin capsules containing the active principle according to the invention, for example 2-(pyridyl-3-methylthio)-pyrimidine hydrochloride:

Composition

| | |
|---|---|
| 2-(pyridyl-3-methylthio)-pyrimidine hydrochloride | 100.0 mg |
| Rape oil | 281.0 mg |
| Beeswax | 2.0 mg |
| Partially hydrogenated vegetable oil | 8.0 mg |
| Soy lecithin | 8.0 mg |
| 3-ethoxy-4-hydroxybenzaldehyde | 1.0 mg |
| Total weight of capsule filling | 400.0 mg |

The substances are mixed, homogenized and processed in the usual way to form soft gelatin capsules.

EXAMPLE 25

Production of dosing aerosols containing the active principle according to the invention, for example 2-(pyridyl-3-methylthio)-pyrimidine hydrochloride:

Composition:

| | |
|---|---|
| 2-(pyridyl-3-methylthio)-pyrimidine hydrochloride | 10.0 mg |
| Sorbitan trioleate | 0.5 mg |
| Difluoromethane | 35.5 mg |
| Dichlorotetrafluoroethane | 25.0 mg |
| Total dose per spray | 71.0 mg |

The substances are dissolved cold and 10 g of solution are introduced into a suitable pressurized-gas pack.

EXAMPLE 26

Production of ampoules containing the active principle according to the invention, for example 2-(pyridyl-3-methylthio)-pyrimidine hydrochloride:

Composition

| | |
|---|---|
| 2-(pyridyl-3-methylthio)-pyrimidine hydrochloride | 100.0 mg |
| Polyethylene glycol 300 | 630.0 mg |
| 1,2-propane diol | 735.0 mg |
| α-tocopherol | 1.0 mg |
| Disodium hydrogen phosphate | 4.0 mg |
| Sodium dihydrogen phosphate | 20.0 mg |
| Water for injection purposes | 610.0 mg |
| Total weight of filling | 2100.0 mg |

The substances are dissolved and the solution obtained is processed in the usual way to form 2 ml ampoules.

What is claimed is:

1. A thiomethyl pyridine compound having the formula

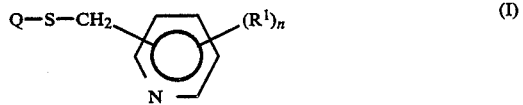

wherein Q is a pyrimidinyl group or a substituted pyrimidinyl group bearing one or two phenyl, naphthyl, halogen, lower alkyl or lower alkoxy substituent, with the proviso that said pyrimidinyl or substituted pyrimidinyl may optionally be condensed with a phenylene radical, a 5- or 6- membered heterocycle which is pyridine, pyrimidine or thiazole or such phenylene radical or heterocycle bearing one or two phenyl, naphthyl, halogen lower alkyl or lower alkoxy substituents, $R^1$ is lower alkyl, halogen, or aminoalkyl, and n is 0 or an integer of from 1 to 4, or a pharmaceutically acceptable salt thereof.

2. The compound according to claim 1, wherein said lower alkyl groups are methyl, ethyl, isopropyl or butyl groups.

3. The compound according to claim 1, wherein said lower alkyl groups are methyl.

4. The compound according to claim 1, wherein said compound is 2-(pyridyl-3-methylthio)-pyrimidine hydrochloride.

5. The compound according to claim 1, wherein said compound is 2-(pyridyl-3-methylthio)-pyrimidine succinate.

6. The compound according to claim 1, wherein said compound is 2-(pyridyl-2-methylthio)-pyrimidine hydrochloride.

7. The compound according to claim 1, wherein said compound is 2-(pyridyl-3-methylthio)-4-methyl-pyrimidine hydrochloride.

8. The compound according to claim 1, wherein said compound is 2-(pyridyl-3-methylthio)-4,6-dimethyl-pyrimidine hydrochloride.

9. The compound according to claim 1, wherein said compound is 2-(pyridyl-4-methylthio)-pyrimidine hydrochloride.

10. The compound according to claim 1, wherein said compound is 2-(pyridyl-6-methyl-3-methylthio)-pyrimidine succinate.

11. The compound according to claim 1, wherein said compound is 2-(pyridyl-2-chloro-3-methylthio)-pyrimidine.

12. The compound according to claim 1, wherein said compound is 2-(pyridyl-3-methylthio-6-chloro)-pyrimidine.

13. The compound according to claim 1, wherein said compound is 4-(pyridyl-3-methylthio)-1-H-pyrazolo-(3,4-d)-pyrimidine.

14. A method for eliciting a bronchosecretolytic or mucolytic response in a mammalian organism in need of such treatment, comprising administering to such organism a bronchosecretolytically or mucolytically effective amount of the thiomethyl pyridine compound as defined by claim 1 or a pharmaceutically effective salt thereof.

15. A method according to claim 14, wherein said method includes administration of said thiomethyl pyridine compound in oral dosage form.

16. A method as claimed in claim 14, wherein said method includes parenteral administration of said thiomethyl pyridine compound.

17. A method for reducing the viscosity of sputum in a mammalian organism in need of such treatment, comprising administering to such organism a bronchosecretolytically or mucolytically effective amount of the thiomethyl pyridine compound as defined in claim 1, or a pharmaceutically effective salt thereof.

18. A method for treating acute or chronic respiratory disease in a mammalian organism in need of such treatment, comprising administrating to such organism a therapeutically effective amount of the thiomethyl pyridine compound as defined in claim 1, or a pharmaceutically effective salt thereof.

19. A method for treating bronchial illness in a mammalian organism, comprising administering to such organism a therapeutically effective amount of the thiomethyl pyridine compound as defined in claim 1, or a pharmaceutically effective salt thereof.

20. A bronchosecretolytic or mucolytic composition of matter, comprising (i) a bronchosecretolytically or mucolytically effective amount of the thiomethyl pyridine compound as defined by claim 1, or a pharmaceutically acceptable salt thereof, and (ii) a pharmaceutically acceptable carrier or diluent thereof.

* * * * *